United States Patent [19]

Braquet et al.

[11] Patent Number: 5,492,906

[45] Date of Patent: Feb. 20, 1996

[54] DERIVATIVES OF THIENO-TRIAZOLO-DIAZEPINE AND THERAPEUTIC COMPOSITIONS CONTAINING THEM

[75] Inventors: Pierre Braquet, Garches; Andre Esanu; Jean-Pierre Laurent, both of Paris; Alain Rolland, Palaiseau, all of France

[73] Assignee: Societe de Conseils de Recherches et d'Applications Scientifiques (S.C.R.A.S.), France

[21] Appl. No.: 837,580

[22] Filed: Feb. 18, 1992

Related U.S. Application Data

[63] Continuation of Ser. No. 730,012, Jul. 12, 1991, abandoned, which is a continuation of Ser. No. 496,421, Mar. 20, 1990, abandoned.

Foreign Application Priority Data

Mar. 31, 1989 [GB] United Kingdom ........................ 07256

[51] Int. Cl.$^6$ .......................... A61K 31/55; C07D 495/22
[52] U.S. Cl. .......................................... 514/21.9; 540/555
[58] Field of Search ............................... 540/555; 514/219

[56] References Cited

FOREIGN PATENT DOCUMENTS 254245  1/1988  European Pat. Off. ................ 540/555

OTHER PUBLICATIONS

Weber, CA 109:129067a (1988).
Burgers Medicinal Chemistry and Drug Discovery, 5th ed. (1995), Wolft, editor, pp. 783–788.
Silverman, The Organic Chemistry of Drug Design and Drug Action, 1992, Academic Press, pp. 19–23.
Burger, *Medicinal Chemistry,* 2nd ed (1960), Interscience Publishers, New York, pp. 72–78.
Noller, *Chemistry of Organic Compounds,* 2nd ed. (1957), p. 272.
Conant et al, *The Chemistry of Organic Compounds,* 5th ed. (1959), p. 333.

*Primary Examiner*—Philip I. Datlow
*Attorney, Agent, or Firm*—Lucas & Just

[57] ABSTRACT

The invention relates to thieno-triazolo-diazepine derivatives of the formula:

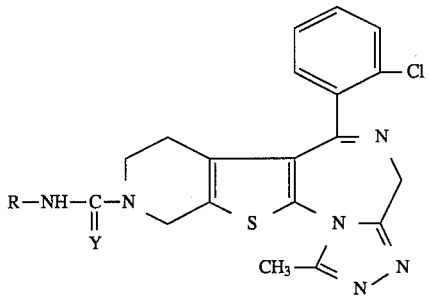

wherein Y stands for oxygen or sulphur and R stands for various substituents, to a preparation process of said compounds and to therapeutic compositions containing the same. The compounds are particularly interesting as anti-asthmatic, anti-allergic and gastro-intestinal protectors.

6 Claims, No Drawings

DERIVATIVES OF THIENO-TRIAZOLO-DIAZEPINE AND THERAPEUTIC COMPOSITIONS CONTAINING THEM

This is a continuation of application Ser. No. 496,421, filed Mar. 20, 1990, now abandoned.

The present invention relates new derivatives of thieno-triazolo-diazepine which are more particularly interesting as anti-asthmatic, anti-allergic agent and gastro-intestinal protectors.

The invention more particularly relates to thieno-triazolo-diazepine derivatives of the formula I:

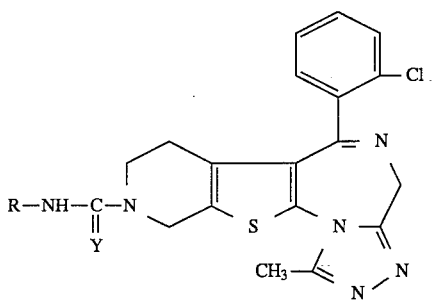

wherein Y stands for oxygen or sulphur and R stands for
- a lower straight alkenyl group up to $C_5$,
- a straight or branched alkyl group up to $C_{20}$, or cyclic up to $C_6$,
- a aryl or hetero-aryl substituted straight or branched alkyl group up to $C_5$,
- a phenyl group substituted by one or several alkyl groups, or lower alkoxy groups up to $C_5$, a phenoxy group, a lower alkyl sulfonyl group up to $C_5$, or fluorine or chlorine atoms, or trifluoromethyl groups or,
- a condensed bicyclic rest containing an hetero-atom and,
- a sulfonyl group substituted by phenyl or by hetero-aryl or by a condensed bicyclic group and, therapeutically acceptable salts thereof.

This invention relates also to a preparation process of said compounds consisting in reacting under nitrogen circulation an excess of thieno-triazolo-diazepine compound of the formula II:

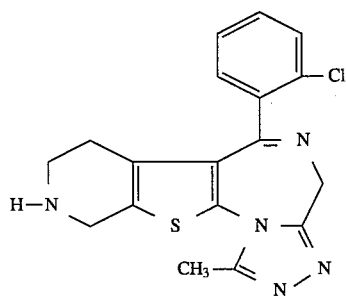

on the appropriate R—N═C═Y derivative wherein R and Y are as above defined, in an aprotic solvent and at a temperature comprised between room temperature and about 70° C. Generally the reaction starts at room temperature but ½ to 3 hours at 60°–70° C. may be necessary to complete the reaction.

The prior art in the field of this invention, may be illustrated by U.S. Pat. No. 4 621 083 (or E.P. 176 927) in which thieno-triazolo-diazepine having PAF-antagonistic activity are disclosed.

This invention relates, finally, to therapeutic compositions containing these compounds.

These new compounds present a PAF-antagonistic activity from ten to thousand times greater than this one of the diazepines disclosed in the above mentionned patent, and also a more potent effectiveness.

The starting material may be obtained by the following sequence of reactions (preparative examples from I to X).

I - (2-chloro)benzoylmethyl cyanide.

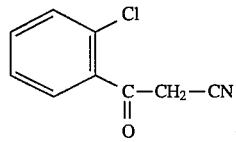

In an appropriate reactor placed under nitrogen circulation at –70° C. were poured 7 1 of anhydrous THF and 115.9 g (1.36 mol) of previously dried cyanoacetic acid. Then were thus added dropwise 1 715 ml (2.74 mol) of 1,6M solution of butyllithium in hexane, while allowing temperature to rise from –70° C. to 0° C. The reactional mixture was then stirred for one hour. Thereafter the reactional mixture was once more cooled at –70° C. and a solution of 120 g (0.685 mol) of chloro-2 benzoyle chloride in 1 1 of anhydrous THF, was added dropwise. After stirring for one hour at always –70° C., the temperature was allowed to rise from –70° C. to 0° C. for one hour. Then there was added dropwise 3 1 of 1N HCl solution and after stirring for a few minutes, the reacted mixture was extracted by chloroform. The organic phase was washed with a 10% aqueous sodium bicarbonate solution, then with a saturated sodium chloride solution, dried, filtered and the solvent was evaporated off to give 135 g of residue. The crystallization was effected by the addition of diisopropyl ether, and the product was filtered off, and washed with hexane to give 97.2 g of the title compound (Yield 79%).

II
-2-amino-3-(2-chlorobenzoyl)-6-(ethoxycarbonyl)-4,5,6,7-tetrahydro-pyrido[3,4-b]thiophene.

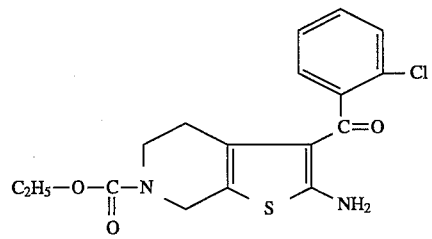

In a two liter-erlen fitted with a cooler, were poured 85.5 g (0.501 mol) of N-carbethoxy-4-piperidone, 90 g (0.501 mol) of (I), 19.3 g (0.600 mol) of flower of sulfur and 44.4 g (0.501 mol) of morpholine, in 550 ml of methanol. The mixture was refluxed for one hour. After evaporation of 250 ml of solvent, the desired compound precipitates, was filtered off, washed with ethanol, then with diethyl ether and dried to yield 155.4 g (85%) of the title compound.

III
-2-(bromoacetamido)-3-(2-chlorobenzoyl)-6-(ethoxy-
carbonyl)-4,5,6,7,-tetrahydro-pyrido[3,4
-b]thiophene.

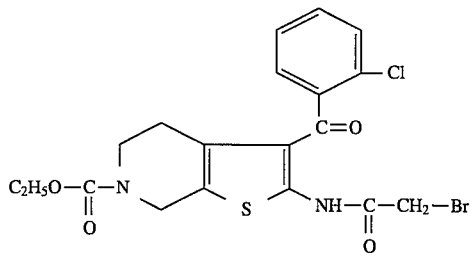

In a five litre-reactor fitted with appropriate means and with separating funnel, were poured 2.5 l of chloroform and 146 g (0.400 mol) of (II). Then, 87.7 g (0.43 mol) of bromoacetylbromide contained in the separating funnel were added dropwise. The reactional mixture was stirred for one hour at room temperature, then washed with 300 ml of icy-water, and the organic phase was dried with anhydrous magnesium sulphate and filtered. The chloroform was evaporated off and the residue was treated with ethanol. The resulting precipitate was filtered off, washed with ethanol, then with diethyl ether, and dried to yield 184.6 g (95%) of the title compound.

IV - 2-(aminoacetamido)-3(2-chlorobenzoyl)-6-
(ethoxycarbonyl)-4,5,6,7
-tetrahydro-pyrido[3,4-b]thiophene.

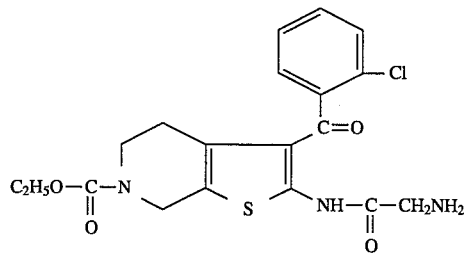

In a five litre-reactor fitted with a gaz-injector were poured 174.8 g (0.36 mol) of (III) and 3 liters of THF. The suspension was cooled at 0° C. and then gazeous ammonia previously dried over potassium hydroxide was added. The addition was conducted in 8 hours. (60 g of ammonia were absorbed). The mixture was stirred overnight at 0° C., then 2 liters of THF was evaporated off under reduced pressure, and 750 ml of ethyl acetate were added. After decantation, the organic phase was washed once with 300 ml of a 10% sodium chloride solution, three times with 300 ml of water, and dried with anhydrous magnesium sulphate. After filtration, the solvent was partially evaporated off at rotavapor. The precipitate was allowed to stand overnight in refrigerator. After filtration, the precipitate was washed with diethyl ether and dried to give 119 g of the title compound. The remaining organic phase was concentrated and treated with a mixture of 1.5 l of diethyl ether/THF (3/1 by volume) to give 14.6 g of the title compound (overall yield 88%).

V -
5-(2-chlorophenyl)-8-(ethoxycarbonyl)-6,7,8,9-tetrahydro-
3H-pyrido[4',3':4,5 ]thieno[3,2-f]1,4-diazepine-2
one.

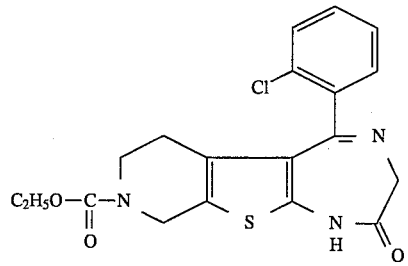

In a two litre-reactor fitted with stirring, cooling and warming means and placed under nitrogen circulation were poured 126.6 g (0.3 mol) (IV) and 800 ml of pyridine. The reaction mixture was refluxed for 18 hours. After having checked that all the starting material had reacted, the pyridine was partially evaporated at a rotavapor under reduced pressure.

The obtained (dark brown) oil was dissolved with 1 litre of ethanol. After cooling in an ice-bath, there was obtained a precipitate which was filtered off, washed with ethanol and diisopropyloxide to yield 101.3 g (83.6%) of the title compound.

VI - 5-(2-chlorophenyl)-8-(ethoxycarbonyl)-6,7,8,9-
tetrahydro-3H-pyrido[4',3':4,5
]thieno[3,2-f]1,4-diazepine-2 thione.

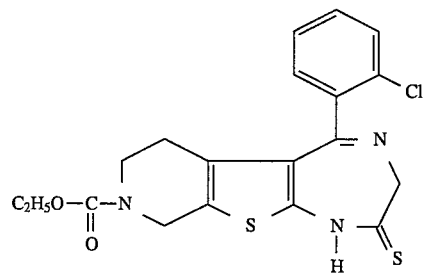

In a three litre-reactor fitted with appropriate means, were poured 93 g (0.230 mol) of V and 1,75 l of pyridine. After solubilization were added 56.3 g (0.25 mol) of phosphorus pentasulphur, and the reaction mixture was then stirred for three hours at 80°–85° C. Thereafter, the pyridine was evaporated off and the obtained residue treated with icy-water. The mixture was then extracted by methylene chloride, dried with anhydrous magnesium sulphate, filtered, evaporated and treated with diethyl-ether. Then the resulting product was filtered off, and treated with 700 ml of acetonitrile. The suspension was heated at 60° C. for 30 minutes and then allowed to cool. After filtration, and washing with acetronitrile, then with diethyl-ether, the residue was dried to yield 80.2 g (83%) of the title compound.

VII - 5-(2-chlorophenyl)-8-(ethoxy carbonyl)-2-hydrazino 6,7,8,9-tetrahydro3H-pyrido[4',3':4,5]thieno [3,2-f]1,4-diazepine.

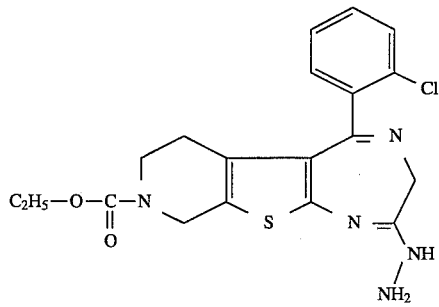

In a two litre-reactor fitted with appropriate means and with separating funnel, were poured 73.5 g (0,175 mol) of VI and 1 l of methanol. Then 26.4 ml (0,525 mol) of hydrazine hydrate contained in the separating funnel, were added at room temperature and the mixture was stirred for two hours at always room temperature. Thereafter 1/7 of methanol were evaporated off at 30° C. and the residue was allowed to crystallize overnight in refrigerator. After filtration, washing with diethyl-ether and drying, there was obtained 65.1 g of the title compound (yield 89%).

VIII
-5-(2-chlorophenyl)-8-(ethoxycarbonyl)-2-acetamido-amino-6,7,8,9,-tetrahydro-3 H-pyrido[4',3':4,5]thieno[3,2-f]1,4-diazepine

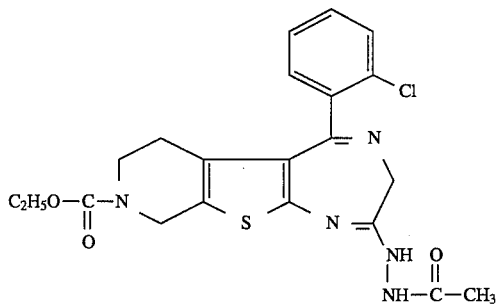

In a two litre reactor fitted with cooling means and placed under nitrogen circulation, were poured 58.5 g (0.140 mol) of VII and 1 l of tetrahydrofuran. Then 11 g (0.140 mol) of acetyl chloride and 150 ml of tetrahydrofuran were added. The addition was conducted in 30 minutes at 0° C. The solution became red after stirring for 45 minutes. The tetrahydrofuran was then evaporated off and the resulting residue treated with icy-water. Then 17.5 g of sodium bicarbonate were added and the mixture was extracted with 1 l of methylene chloride. The organic phase was washed once with water and dried with anhydrous magnesium sulphate. After filtration, the solvent was evaporated off and the resulting residue treated with diethyl-ether, filtered and dried to yield 54.1 g (84%) of the title compound.

IX -6-(2-chlorophenyl)-9-(ethoxycarbonyl)-7,8,9,10-tetrahydro-1-methyl-4H-pyrido[4',3':4,5]thieno [3,2-f]1,2,4-triazolo[4,3-a]1,4-diazepine.

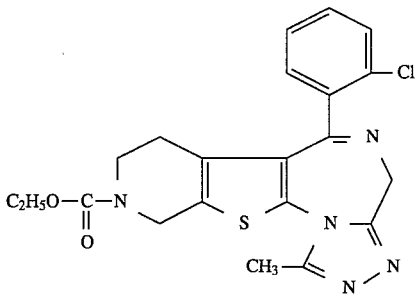

In a two litre-reactor fitted with appropriate means and placed under nitrogen circulation, were poured 750 ml of acetic acid and 46.9 g (0.102 mol) of VIII. The (red) solution was slowly warmed over one hour to reflux temperature and the reflux was thus maintained for 15 minutes. The (yellow) solution was then concentrated at rotavapor at a bath temperature not exceeding 35° C., and the acetic acid was extracted off with 700 ml of toluene. The residue was then treated with diethyl-ether, filtered, washed with diethyl-ether, and dried to yield 42.8 g (95%) of the title compound.

X - 6-(2-chlorophenyl)-7,8,9,10-tetrahydro-1-methyl4H-pyrido[4',3':4,5]thieno[3,2-f]1,2,4-triazolo[4,3-a]1,4-diazepine.

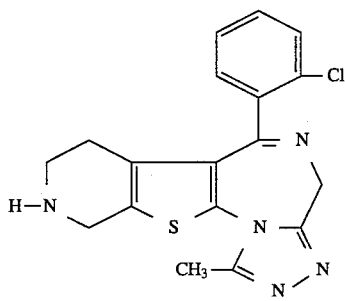

In a one litre-reactor fitted with appropriate means, were poured 500 ml of mixture of bromhydric acid/acetic acid (30% bromhydric acid by volume). Then 35.8 g (0,081 mol) of IX were added portionwise at 5° C. and the mixture was then stirred at room temperature for five days (CCM analysis showed traces of starting material). Thereafter, 250 ml of acetic acid were evaporated off and the compound precipitated. Then 250 ml of diethyl-ether were added and the mixture was stirred for 30 minutes. The precipitate was filtered off, washed with diethyl-ether and poured into a one litre-flask in which 500 ml of icy-water were added. The pH was ajusted at pH 9.5 with addition of a 40% aqueous sodium hydroxide solution. The reaction mass temperature was maintained below 20° C. After extraction with dichloromethane, the organic phase was dried with anhydrous magnesium sulphate, filtered and the dichloromethane was partially evaporated off. Then 120 ml of ethyl acetate were added with stirring. After precipitation, 160 ml of diethyl-ether was added and the mixture was allowed to crystallize overnight in refrigerator. After filtration and washing with diethyl-ether, there was obtained 28.1 g of the title compound (yield 93,6%).

The invention will be better understood from the description of the following examples.

EXAMPLE 1

6-(2-chlorophenyl)-9-isopropylthiocarbamoyl-7,8,9,10-tetrahydro-1-methyl4 H-pyrido[4',3':4,5]thieno[3,2 -f]1,2,4-triazolo[4,3-a]1,4-diazepine Y=S R=-isopropyl- In a 1 litre reactor, under nitrogen circulation are poured 650 ml of pure benzene, 26.85 g ( 172 mMoles) of 6-(2-chlorophenyl) 7,8,9,10-tetrahydro-1-methyl4H-pyrido [4',3',:4,5]thieno [3-2-f] 1,2,4-triazolo [4,3-a] 1,4-diazepine, then dropwise a solution of 7.6 g (75 mM) of isopropylisothiocyanate, dissolved in 25 ml of pure benzene. The addition is conducted in about 15 minutes and the temperature rises from 15° to 25° C. After stirring the reacting mixture 3 hours at room temperature, it is heated at then 60°–70° C., then refluxed for 15 minutes. After cooling, filtration, washing with benzene, washing twice with diethylether, the compound is dried, then dissolved in 250 ml of acetone and refluxed for about 15 minutes. After cooling filtration, twice washing with acetone and twice washing with diethylether, the compound is separated, dried overnight at 60° C. under reduced pressure. There is obtained 34 g of the title compound (Yield 91%). Melting point 205°–206° C. (Tottoli); white powder.

The following compounds have been prepared as described in example 1, but starting with the appropriate carbamoyl derivative.

EXAMPLE 2

6-(2-chlorophenyl)-9-isopropylcarbamoyl-7,8,9,10-tetrahydro-1-methyl4H-pyrido[4',3':4,5 ]thieno[3,2-f]1,2,4-triazolo [4,3-a] 1,4-diazepine Y=O R=isopropyl-M.p.:214° C. (Tottoli); white powder.

EXAMPLE 3

6-(2-chlorophenyl)-9-tertbutylcarbamoyl-7,8,9,10-tetrahydro-1-methyl4 H-pyrido[4',3':4,5]thieno[3,2-f]1,2,4-triazolo [4,3-a]1,4-diazepine Y=O R=tertbutyl-M.p.:240°–245° C. (Tottoli); white powder.

EXAMPLE 4

6-(2-chlorophenyl)-9-tertbutylthiocarbamoyl-7,8,9,10-tetrahydro-1-methyl4 H-pyrido[4',3':4,5]theno [3,2-f]1,2,4-triazolo[4,3-a]1,4-diazepine Y=S R=tertbutyl-M.p.:189° C. (Tottoli); white powder.

EXAMPLE 5

6-(2-chlorophenyl)-9-hexadecylthiocarbamoyl-7,8,9,10-tetrahydro-1-methyl4 H-pyrido[4',3':4,5]thieno [3,2-f]1,2,4-triazolo [4,3-a]1,4-diazepine Y=S R=hexadecyl-M.p.:168°–170° C. (Tottoli); amorphous white powder.

EXAMPLE 6

6-(2-chlorophenyl)-9-(4-methoxy)phenylcarbamoyl-7,8,9,10-tetrahydro-1-methyl 4H-pyrido[4',3':4,5]thieno[3,2-f] 1,2,4-triazolo[4,3-a]1,4-diazepine Y=O R=(4-methoxy)phenyl-M.p.:202° C. (Tottoli); cream-white powder.

EXAMPLE 7

6-(2-chlorophenyl)-9-(4-methoxy)phenylthiocarbamoyl-7,8,9,10-tetrahydro-1-methyl4 H-pyrido[4',3':4,5]thieno[3,2-f]1,2,4-triazolo[4,3-a]1,4-diazepine Y=S R=(4-methoxy)phenyl-M.p.:197°–204° C. (Tottoli); pale beige powder.

EXAMPLE 8

6-(2-chlorophenyl)-9-(3,4,5-trimethoxy)phenylcarbamoyl-7,8,9,10-tetrahydro-1-methyl 4H-pyrido[4',3':4,5]thieno [3,2-f]1,2,4-triazolo [4,3-a]1,4-diazepine Y=O R=(3,4,5-trimethoxy)phenyl-M.p.:176°–179° C. (Tottoli); cream-white powder.

EXAMPLE 9

6-(2-chlorophenyl)-9-(3,4,5-trimethoxy)phenylthiocarbamoyl-7,8,9,10-tetrahydro-1-methyl 4H-pyrido[4',3':4,5]thieno [3,2-f]1,2,4-triazolo[4,3-a]1,4-diazepine Y=S R=(3,4,5-trimethoxy)phenyl-M.p.:184° C. (Tottoli); white powder.

EXAMPLE 10

6-(2-chlorophenyl)-9-(4-tertbutyl)phenylcarbamoyl-7,8,9,10-tetrahydro-1-methyl 4H-pyrido[4',3':4,5]thieno [3,2-f] 1,2,4-triazolo[4,3-a]1,4-diazepine Y=O R=(4-tertbutyl)phenyl-M.p.:218°–220° C. (Tottoli); cream-white powder.

EXAMPLE 11

6-(2-chlorophenyl)-9-(4-tertbutyl)phenylthiocarbamoyl-4H-pyrido[4',3':4,5]thieno [3,2-f]1,2,4-triazolo[4,3-a]1,4-diazepine Y=S R=(4-tertbutyl)phenyl-M.p.:225°–226° C. (Tottoli); white powder.

EXAMPLE 12

6-(2-chlorophenyl)-9-(2-trifluoromethyl)phenylthiocarbamoyl-7,8,9,10-tetrahydro-1-methyl 4H-pyrido[4',3':4,5]thieno[3,2-f]1,2,4-triazolo[4,3-a]1,4-diazepine Y=S R=(2-trifluoromethyl)phenyl-M.p.:179°–180° C. (Tottoli); white powder.

EXAMPLE 13

6-(2-chlorophenyl)-9-(3-trifluoromethyl)phenylthiocarbamoyl-7,8,9,10-tetrahydro-1-methyl 4H-pyrido[4',3':4,5]thieno[3,2-f]1,2,4-triazolo[4,3-a]1,4-diazepine Y=S R=(3-trifluoromethyl)phenyl-M.p.:169°–170° C. (Tottoli); white powder.

EXAMPLE 14

6-(2-chlorophenyl)-9-(4-trifluoromethyl)phenylcarbamoyl-7,8,9,10-tetrahydro-1-methyl 4H-pyrido[4',3':4,5]thieno [3,2-f]1,2,4-triazolo[4,3-a]1,4-diazepine Y=O R=(4-trifluoromethyl)phenyl-M.p.:212°– 217° C. (Tottoli); pale beige powder.

EXAMPLE 15

6-(2-chlorophenyl)-9 -(4-trifluoromethyl)phenylthiocarbamoyl-7,8,9,10-tetrahydro-1-methyl 4H-pyrido[4',3':4,5]thieno[3,2-f]1,2,4-triazolo[4,3-a]1,4-diazepine Y=S R=(4-trifluoromethyl)phenyl-M.p.:178°–180° C. (Tottoli); white powder.

EXAMPLE 16

6-(2-chlorophenyl)-9-(4-fluoro)phenylthiocarbamoyl-7,8,9,10-tetrahydro-1-methyl 4H-pyrido[4',3':4,5]thieno[3,2-f]1,2,4-triazolo[4,3-a]1,4-diazepine Y=S R=(4-

EXAMPLE 17

6-(2-chlorophenyl)-9-(2,3-dichloro)phenylcarbamoyl-7,8,9,10-tetrahydro-1-methyl 4H-pyrido[4',3':4,5]thieno[3,2-f]1,2,4-triazolo[4,3-a]1,4-diazepine   Y=O   R=(2,3-dichloro)phenyl-M.p.:200°–204° C. (Tottoli); white powder.

EXAMPLE 18

6-(2-chlorophenyl)-9-(4-phenoxy)phenylcarbamoyl-7,8,9,10-tetrahydro-1-methyl 4H-pyrido[4',3':4,5 ]thieno[3,2-f]1,2,4-triazolo[4,3-a]1,4-diazepine   Y=O   R=(4-phenoxy)phenyl-M.p.:187°–193° C. (Tottoli); white powder.

EXAMPLE 19

6-(2-chlorophenyl)-9-(α-methyl)phenethylthiocarbamoyl-7,8,9,10-tetrahydro-1-methyl 4H-pyrido[4',3':4,5]thieno[3,2-f]1,2,4-triazolo[4,3-a]1,4-diazepine   Y=S   R=(α-methyl)phenethyl-M.p.:210°–214° C. (Tottoli); white powder.

EXAMPLE 20

6-(2-chlorophenyl)-9-(β-methyl)phenethylthiocarbamoyl-7,8,9,10-tetrahydro-1-methyl 4H-pyrido[4',3':4,5]thieno[3,2-f]1,2,4-triazolo[4,3-a]1,4-diazepine   Y=S   R=(β-methyl)phenethyl-M.p.:200° C. (Tottoli); cream-white powder.

EXAMPLE 21

6-(2-chlorophenyl)-9-(4-methylsulfonyl)phenylthiocarbamoyl-7,8,9,10-tetrahydro-1-methyl 4H-pyrido[4',3':4,5]thieno[3,2-f]1,2,4-triazolo[4,3-a]1,4-diazepine   Y=S   R=(4-methylsulfonyl)phenyl-M.p.:214°–215° C. (Tottoli); pale beige powder.

EXAMPLE 22

6-(2-chlorophenyl)-9-(2,4-diterbutyl)phenylthiocarbamoyl-7,8,9,10-tetrahydro-1-methyl 4 H-pyrido[4',3':4,5]thieno[3,2-f]1,2,4-triazolo[4,3-a]1,4-diazepine Y=S R=(2,4-diterbutyl)phenyl-M.p.:146°–148° C. (Tottoli); pale beige powder.

EXAMPLE 23

6-(2-chlorophenyl)-9-benzylcarbamoyl-7,8,9,10-tetrahydro-1-methyl-4H-pyrido[4',3':4,5 ]thieno[3,2-f]1,2,4-triazolo[4,3-a]1,4-diazepine Y=O R=benzyl-M.p.:246°–249° C. (Tottoli); cream-white powder.

EXAMPLE 24

6-(2-chlorophenyl)-9-(2-furfuryl)thiocarbamoyl-7,8,9,10-tetrahydro-1-methyl-4 H-pyrido[4',3':4,5]thieno[3,2-f]1,2,4-triazolo[4,3-a]1,4-diazepine   Y=S   R=(2-furfuryl)-M.p.:174° C. (Tottoli); pale yellow powder.

EXAMPLE 25

6-(2-chlorophenyl)-9-(3-quinolyl)thiocarbamoyl-7,8,9,10-tetrahydro-1-methyl-4 H-pyrido[4',3':4,5]thieno[3,2-f]1,2,4-triazolo[4,3-a]1,4-diazepine   Y=S   R=(3-quinolyl)-M.p.:192°–193° C. (Tottoli); pale beige powder.

EXAMPLE 26

6-(2-chlorophenyl)-9-cyclohexylthiocarbamoyl-7,8,9,10-tetrahydro-1-methyl 4 H-pyrido[4',3':4,5]thieno[3,2-f]1,2,4-triazolo[4,3-a]1,4-diazepine   Y=S   R=cyclohexyl-M.p.:209°–214° C. (Tottoli); white powder.

EXAMPLE 27

6-(2-chlorophenyl)-9-cyclohexylcarbamoyl-7,8,9,10-tetrahydro-1-methyl-4H-pyrido[4', 3':4,5]thieno[3,2-f]1,2,4-triazolo[4,3-a]1,4-diazepine Y=O R=cyclohexyl-M.p.:220° C. (Tottoli); cream-white powder.

EXAMPLE 28

6-(2-chlorophenyl)-9-allylthiocarbamoyl-7,8,9,10-tetrahydro-1-methyl-4 H-pyrido[4',3':4,5]thieno[3,2-f]1,2,4-triazolo[4,3-a]1,4-diazepine Y=S R=allyl-M.p.:224°–226° C. (Tottoli); cream-white powder.

EXAMPLE 29

6-(2-chlorophenyl)-9-(2,4-difluoro)phenylcarbamoyl-7,8,9,10-tetrahydro-1-methyl-4H-pyrido [4',3':4,5]thieno[3,2-f]1,2,4-triazolo[4,3-a]1,4-diazepine   Y=O   R=(2,4-difluoro)phenyl-M.p.:245°–250° C. (Tottoli); white powder.

EXAMPLE 30

6-(2-chlorophenyl)-9-(phenylsulfonyl)thiocarbamoyl-7,8,9,10-tetrahydro-1-methyl-4 H-pyrido[4',3':4,5]thieno[3,2-f]1,2,4-triazolo[4,3-a]1,4-diazepine Y=S R=phenylsulfonyl-M.p.:205° C. (Tottoli); white powder.

EXAMPLE 31

6-(2-chlorophenyl)-9-(2-furylsulfonyl)thiocarbamoyl-7,8,9,10-tetrahydro-1-methyl-4 H-pyrido[4',3':4,5]thieno[3,2-f]1,2,4-triazolo[4,3-a]1,4-diazepine   Y=S   R=2-(furyl)sulfonyl-M.p.:222°–226° C. (Tottoli); pale beige powder.

EXAMPLE 32

6-(2-chlorophenyl)-9-(2-thienylsulfonyl)carbamoyl-7,8,9,10-tetrahydro-1-methyl-4 H-pyrido[4',5':4,5]thieno[3,2-f]1,2,4-triazolo[4,3-a]1,4-diazepine Y=O R=2-(thienyl)sulfonyl-M.p.:233° C. (Tottoli); white powder.

EXAMPLE 33

6-(2-chlorophenyl)-9-(2-pyrrolylsulfonyl)thiocarbamoyl7,8,9,10-tetrahydro-1-methyl-4 H-pyrido[4',3':4,5]thieno[3,2-f]1,2,4-triazolo[4,3-a]1,4-diazepine   Y=S   R=2-(pyrrolyl)sulfonyl-M.p.:211°–213° C. (Tottoli); white powder.

EXAMPLE 34

6-(2-chlorophenyl)-9-(3-pyridylsulfonyl)carbamoyl-7,8,9,10-tetrahydro-1-methyl-4 H-pyrido[4',3':4,5]thieno[3,2-f]1,2,4-triazolo[4,3-a]1,4-diazepine   Y=O   R=3-(pyridyl)sulfonyl-M.p.:184°–189° C. (Tottoli); beige powder.

EXAMPLE 35

6-(2-chlorophenyl)-9-(4-quinolylsulfonyl)thiocarbamoyl-7,8,9,10-tetrahydro-1-methyl-4 H-pyrido[4',3':4,5]thieno[3,2-f]1,2,4-triazolo[4,3-a]1,4-diazepine   Y=S   R=4-(quinolyl)sulfonyl-M.p.:240°–253° C. (Tottoli); white powder.

EXAMPLE 36

6-(2-chlorophenyl)-9-(4-morpholinylsulfonyl)carbamoyl-7,8,9,10-tetrahydro-1-methyl-4 H-pyrido[4',3':4,5]thieno[3,2-f]1,2,4-triazolo[4,3-a]1,4-diazepine Y=O R=4-(morpholinyl)sulfonyl-M.p.:207°–211° C. (Tottoli); white powder.

TOXICITY

The compounds of the invention are not toxic on the mice per os at the dose of 1 g/kg. By the IP route on the mice, only the compounds of examples 10, 17, 18 and 33 presented a LD 50 comprised between 0.4 and 1 g/kg and all the other were not toxic at 1 g/kg.

PHARMACOLOGY

Various pharmacological determinations have been made on these compounds; they are summarized as follows:
1) Inhibition of platelet agregation induced by PAF This experimentation was conducted according to the method of R. KINLOUGH. RATHBONE, J. P. CAZENAVE, M. PACKHAM and F. MUSTARD, Lab. Invest. 48, 98, 1980. In this test, New Zealand rabbits were used (male New Zealand rabbits of an average weight of 5 kg).

The determinations are made on a chrono-log Coultronics agregometer, at 57° C. coupled with a graphic recorder; the results of these determinations (in molecular concentration) are reported on the table I on the central column.
2) Inhibition of the binding to benzodiazepine receptors The interest of the previous experimentation depends on the results obtained in this experimentation: as a compound of the invention has a benzodiazepine like structure, it is important to check whether the specific benzodiazepine activity would not appear at the dose where platelet agregation was inhibited.

Therefore, this experimentation has been conducted according to the method of MOHLER H. and RICHARD J. G. Agonist and antagonist benzodiazepine receptor intereaction in vitro, Nature, vol. 294, 763°–765, 1981.

This experimentation was conducted on rat brains incubated 1 h 30 at 4° C. using $^3$H-RO-15-4788 and $^3$H-RO-5-4864 (NEN) as tracers and RO-15-4788 and RO-5-4864 as reference antagonists.

The results in molecular concentration are reported in the table I, on the right hand column.
3) Action on the bronchospasm induced by the PAF The PAF intravenous injection in anaesthetized guinea-pigs induces a bronchoconstriction with a leucopeny and a thrombocytopeny, according to the method described in S. DESQUAND, C. TOUVAY, J. RANDON, V. LAGENTE, B. VILAIN, I. MARIDONNEAU-PARINI, A. ETIENNE, J. LEFORT, P. BRAQUET and B. VARGAFTIG. Interference of BN 52021 (Ginkolide B) with the bronchopulmonary effects of PAF-acether in the guinea-pig. Eur. J. Pharmacol. 127: 83–95, 1986.

Male Hartley guinea-pigs (400–450 g) (Charles River) anaesthetized with urethane (2 g/kg IP), then are thracheotomized and submitted to a forced respiration with a breathing pump:70–80 strokes/mn, 1 ml of air/ 100 g per stroke. A catheter is introduced in the jugular vein for the injections, an other is introduced in the carotic artery for blood takings. The initial resistance is kept constant under the pressure of 10 cm of water in accordance with the Konzett and Rössler method and the air in excess is measured with a transducor for bronchospasm UGO BASILE together with an enregistror GEMINI. The guinea-pigs had received an IV injection of pancuronium (Pavulon) to inhibit their spontaneous respiration.

The compound according to the invention and the reference compound WEB 2086 (see the above cited Boehringer patent) have been prepared as suspension in gummy water and administrated orally 1 hour before the stimulation by the PAF.

The bronchoconstriction is appreciated by the calculation of the percentage of bronchoconstriction $$\frac{A}{B} \times 100$$

wherein A stands for induced bronchoconstriction in mm and B stands for maximum bronchoconstriction in mm.

The results are reported on table II.

PRESENTATION - POSOLOGY

In human therapy, the compounds of the invention are preferably administered by oral route. Prefered forms of administration include tablets, gelatine capsules and the like. Usual posology is from 50 mg to 500 mg per diem according to the case.

Prefered unit dose is 50 mg, associated with appropriate carriers and agents.

TABLE IA

| EXAMPLES | $IC_{50}$ | BDZ receptors |
| --- | --- | --- |
| 1 | $3.28 \times 10^{-8}$ | $7 \times 10^{-6}$ |
| 2 | $2.35 \times 10^{-8}$ | $6.6 \times 10^{-5}$ |
| 3 | $1.71 \times 10^{-8}$ | $4.3 \times 10^{-7}$ |
| 4 | $8.82 \times 10^{-9}$ | $1.35 \times 10^{-7}$ |
| 5 | $2.97 \times 10^{-7}$ | $6.3 \times 10^{-5}$ |
| 6 | $1.27 \times 10^{-7}$ | $7.7 \times 10^{-5}$ |
| 7 | $3.01 \times 10^{-7}$ | $2 \times 10^{-6}$ |
| 8 | $1.15 \times 10^{-8}$ | $1.5 \times 10^{-6}$ |
| 9 | $3.87 \times 10^{-8}$ | $4.5 \times 10^{-6}$ |
| 10 | $8.8 \times 10^{-9}$ | $5.25 \times 10^{-6}$ |
| 11 | $9.44 \times 10^{-9}$ | $1.2 \times 10^{-6}$ |
| 12 | $1.71 \times 10^{-7}$ | $3.5 \times 10^{-6}$ |

All values expressed are molecular concentration.

TABLE IB

| EXAMPLES | $IC_{50}$ | BDZ receptors |
| --- | --- | --- |
| 13 | $1.71 \times 10^{-7}$ | $6.25 \times 10^{-6}$ |
| 14 | $1.5 \times 10^{-7}$ | $7.05 \times 10^{-5}$ |
| 15 | $2.2 \times 10^{-7}$ | $1.25 \times 10^{-6}$ |
| 16 | $6.4 \times 10^{-8}$ | $7. \times 10^{-7}$ |
| 17 | $5.5 \times 10^{-8}$ | $9.2 \times 10^{-7}$ |
| 18 | $3.3 \times 10^{-8}$ | $8.6 \times 10^{-7}$ |
| 19 | $4.25 \times 10^{-8}$ | $3.6 \times 10^{-7}$ |
| 20 | $6.17 \times 10^{-9}$ | $7.2 \times 10^{-7}$ |
| 21 | $2.4 \times 10^{-8}$ | $1.1 \times 10^{-6}$ |
| 22 | $3.66 \times 10^{-7}$ | $6.3 \times 10^{-7}$ |
| 23 | $6.68 \times 10^{-8}$ | $1.6 \times 10^{-6}$ |
| 24 | $4.8 \times 10^{-8}$ | $6.5 \times 10^{-7}$ |

All values expressed are molecular concentration.

TABLE IC

| EXAMPLES | $IC_{50}$ | BDZ receptors |
| --- | --- | --- |
| 25 | $1.82 \times 10^{-7}$ | $3.5 \times 10^{-7}$ |
| 26 | $5.33 \times 10^{-8}$ | $4.1 \times 10^{-6}$ |

TABLE IC-continued

| EXAMPLES | IC$_{50}$ | BDZ receptors |
|---|---|---|
| 27 | $4.52 \times 10^{-8}$ | $2. \times 10^{-6}$ |
| 28 | $9.05 \times 10^{-9}$ | $1.4 \times 10^{-7}$ |
| 29 | $5.86 \times 10^{-8}$ | $2.2 \times 10^{-7}$ |
| 30 | $1.1 \times 10^{-8}$ | $6.3 \times 10^{-7}$ |
| 31 | $8.15 \times 10^{-9}$ | $6.15 \times 10^{-7}$ |
| 32 | $6.66 \times 10^{-8}$ | $4.33 \times 10^{-6}$ |
| 33 | $2.05 \times 10^{-7}$ | $9.1 \times 10^{-6}$ |
| 34 | $1.0 \times 10^{-7}$ | $4. \times 10^{-5}$ |
| 35 | $3.4 \times 10^{-8}$ | $2.2 \times 10^{-6}$ |
| 36 | $6.10 \times 10^{-9}$ | $7.25 \times 10^{-6}$ |

All values expressed are molecular concentration.

TABLE II

| Examples | Percentage of bronchoconstriction | Percentage of action |
|---|---|---|
| Controls | 79. ± 5.55 | — |
| WEB 2086 | 25.3 ± 11.56*** | −68.0 |
| 1 | 23.4 ± 10.50*** | −70.4 |
| 3 | 28.7 ± 9.30*** | −63.7 |
| 5 | 30.3 ± 8.80*** | −61.6 |
| 7 | 13 ± 4.39*** | −83.5 |
| 8 | 16.2 ± 8.38*** | −79.5 |
| 10 | 26.7 ± 11.0*** | −66.2 |
| 14 | 48.6 ± 14.32** | −38.5 |
| 18 | 14.1 ± 11.25*** | −81.8 |
| 22 | 25.5 ± 13.2*** | −67.7 |
| 24 | 33.3 ± 12.8*** | −57.9 |
| 30 | 37.2 ± 14.95*** | −52.9 |
| 33 | 22.4 ± 9.8*** | −71.7 |

We claim:

1. A thieno-triazolo-diazepine compound of the formula:

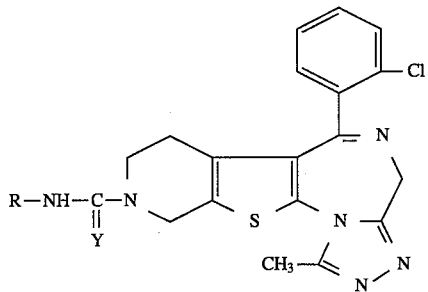

wherein, Y stands for sulfur and R stands for
a lower straight alkenyl group up to $C_5$,
a straight or branched alkyl group up to $C_{20}$, or cyclic up to $C_6$,
an aryl or furyl substituted straight or branched alkyl group up to $C_5$,
a phenyl group substituted by one or several alkyl groups, or lower alkoxy groups up to $C_5$, a phenoxy group, a lower alkyl sulfonyl group up to $C_5$, or fluorine or chlorine atoms, or trifluoromethyl groups,
a quinolyl, or
a sulfonyl group substituted by phenyl or by furyl, thienyl, pyrrolyl, pyridinyl, morpholinyl, or quinolyl; or therapeutically acceptable salts thereof;
or Y stands for oxygen and R stands for-4)
a lower straight alkenyl group up to $C_5$,
a straight or branched alkyl group up to $C_{20}$,
a furyl substituted straight or branched alkyl group up to $C_5$,
a phenyl group substituted by one or several alkyl groups, or lower alkoxy groups up to $C_5$, a phenoxy group, a lower alkyl sulfonyl group up to $C_5$, or fluorine or chlorine atoms, or trifluoromethyl groups,
a quinolyl, or
a sulfonyl group substituted by phenyl or by furyl, thienyl, pyrrolyl, pyridinyl, morpholinyl, or quinolyl; or
therapeutically acceptable salts thereof.

2. A therapeutic composition of matter comprising as an active ingredient therein a sufficient amount of one or more of the compounds according to claim 1 associated with carriers suitable for the selected administration form.

3. The therapeutic composition according to claim 2, for oral administration, containing from 10 to 100 mg of active ingredient per dose unit.

4. Thieno-triazolo-diazepine derivatives of the formula:

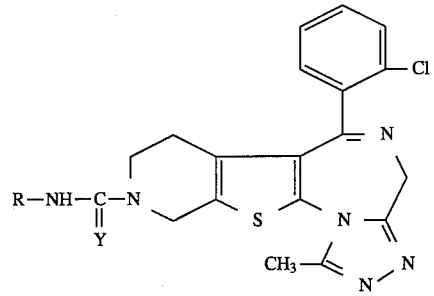

wherein Y stands for oxygen or sulfur and R stands for
a lower straight alkenyl group up to $C_5$,
a straight or branched alkyl group up to $C_{20}$,
a furyl substituted straight or branched alkyl group up to $C_5$,
a phenyl group substituted by one or several alkyl groups, or lower alkoxy groups up to $C_5$, a phenoxy group, a lower alkyl sulfonyl group up to $C_5$, or fluorine or chlorine atoms, or trifluoromethyl groups or,
a quinolyl or,
a sulfonyl group substituted by phenyl or by furyl, thienyl, pyrrolyl, pyridinyl, morpholinyl or by quinolyl or therapeutically acceptable salts thereof.

5. A therapeutic composition of matter comprising as an active ingredient therein a sufficient amount of one or more of the compounds according to claim 4 associated with carriers suitable for the selected administration form.

6. The therapeutic composition according to claim 5 for oral administration, containing from 10 to 100 mg of active ingredient per dose unit.

* * * * *

UNITED STATES PATENT AND TRADEMARK OFFICE
CERTIFICATE OF CORRECTION

PATENT NO. : 5,492,906
DATED : February 20, 1996
INVENTOR(S) : Pierre Braquet et al.

It is certified that error appears in the above-indentified patent and that said Letters Patent is hereby corrected as shown below:

Column 1, line 7, after "relates" insert --to--; line 9, change "agent" to --agents--; line 30, change "a" to --an--; line 65, change "are" to --is--.

Column 2, line 2, after "to" insert --a--; line 3, change "mentionned" to --mentioned--; line 23, after "allowing" insert --the--; line 24, change "reactional" to --reaction--; line 25, change "reactional" to --reaction--; line 27, change "benzoyle" to --benzoyl--; line 63, change "(0,501" to --(0.501)--

Column 3, line 48, change "gaz-injector" to --gas-injector--; line 51, change "gazeous" to --gaseous--; line 60, change "at" to --in a--.

Column 4, line 24, change "at" to --in--.

Column 5, line 21, change "(0,175" to --(0.175--; line 22, change "(0,525" to --(0.525--.

Column 6, line 48, change "(0,081" to --(0.081--.

Column 7, line 46, change "theno" to --thieno--.

Column 8, line 29, before "4H" insert --7,8,9,10-tetrahydro-1-methyl--.

Column 11, line 22, change "agregation" to --aggregation--; line 57, change "(Ginkolide" to --(Gingkolide--; line 61, before "anaesthetized" insert --are--; line 65, change "an other" to --another--.

UNITED STATES PATENT AND TRADEMARK OFFICE
CERTIFICATE OF CORRECTION

PATENT NO. : 5,492,906
DATED : February 20, 1996
INVENTOR(S) : Pierre Braquet et al.

It is certified that error appears in the above-indentified patent and that said Letters Patent is hereby corrected as shown below:

Column 12, line 2, change "transducor" to --transducer--; line 24, change "Prefered" to --Preferred--; line 25, change "gelatine" to --gelatin--; line 28, change "Prefered" to --Preferred--.

Column 14, line 2 (claim 1), change "for-4)" to --for--.

Signed and Sealed this

Ninth Day of July, 1996

Attest:

BRUCE LEHMAN

Attesting Officer

Commissioner of Patents and Trademarks